United States Patent [19]

Fukuda

[11] Patent Number: 4,676,245
[45] Date of Patent: Jun. 30, 1987

[54] INTERLOCKING SURGICAL STAPLE ASSEMBLY

[76] Inventor: Mamoru Fukuda, 1260 Hardy, Bridge City, Tex. 77611

[21] Appl. No.: 781,101

[22] Filed: Sep. 26, 1985

Related U.S. Application Data

[63] Continuation of Ser. No. 465,246, Feb. 9, 1983, abandoned.

[51] Int. Cl.[4] .............................................. A61B 17/08
[52] U.S. Cl. ............................ 128/334 C; 128/334 R; 128/335; 227/DIG. 1
[58] Field of Search ................... 128/334 R, 335, 336, 128/337; 227/DIG. 1 A–DIG. 1 C

[56] References Cited

U.S. PATENT DOCUMENTS

| | | | |
|---|---|---|---|
| 655,190 | 8/1900 | Bramson | 128/335 |
| 1,452,372 | 4/1923 | Gomez | 128/335 |
| 2,811,971 | 11/1957 | Scott | 128/335 |
| 3,068,869 | 12/1962 | Sheldon et al. | 128/337 |
| 3,357,296 | 12/1967 | Lefever | 227/DIG. 1 |
| 3,385,299 | 5/1968 | LeRoy | 128/337 |
| 3,516,409 | 6/1970 | Howell | 604/179 |
| 3,568,276 | 3/1971 | Morgan | 128/335 |
| 3,863,640 | 2/1975 | Haverstock | 128/335 |
| 4,259,959 | 4/1981 | Walker | 128/337 |
| 4,430,998 | 2/1984 | Harvey et al. | 128/335 |
| 4,467,805 | 8/1984 | Fukuda | 128/335 |

Primary Examiner—C. Fred Rosenbaum
Assistant Examiner—Gene B. Kartchner

[57] ABSTRACT

A skin opening and closure device for surgical procedures incorporates elongated flexible locking strips having elongated locking means formed thereon which is adapted to be placed in interlocking assembly and capable of being separated and relocked, as desired. A plurality of half staples are provided, each of which is partially embedded within respective ones of the locking strips to thereby define staple assemblies. The half-staples incorporate curved, hook-like skin penetrating elements which retain the locking strips in positive hooked assembly with the skin to prevent inadvertent staple separation when the locking strips are separated. The half-staples are adapted to be bent intermediate the extremities thereof to establish a secure skin retaining relation with the skin of the patient to provide a secure closure at the surgical incision. In use, the half-staples of the device are brought into engaging assembly with the skin of the patient at the site of the intended incision. Thereafter, the locking strips are separated in zipper-like manner to expose the skin for incision. After completion of the surgical procedure, the locking strips are brought into interlocked relation by manual pressure or by zipper-like closure means to close the incision.

8 Claims, 7 Drawing Figures

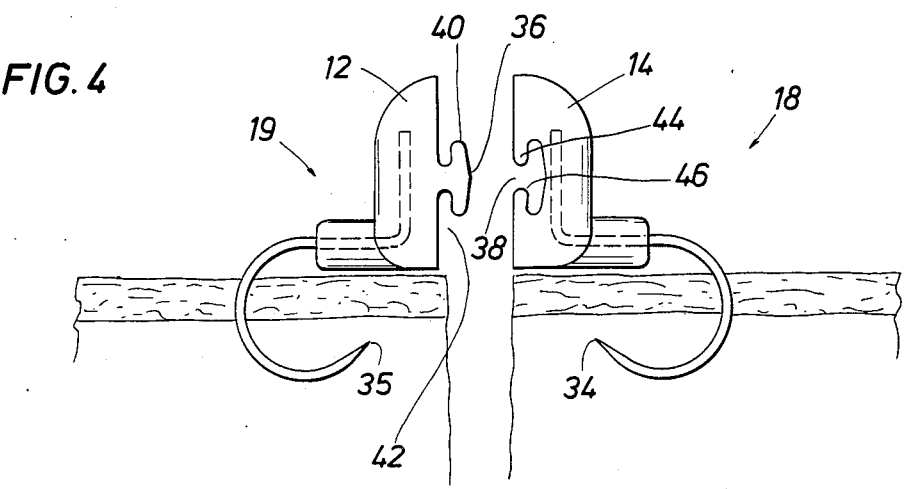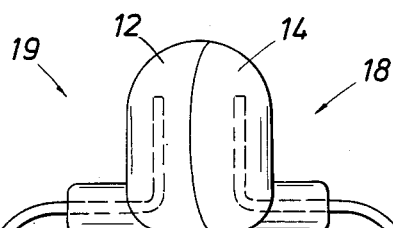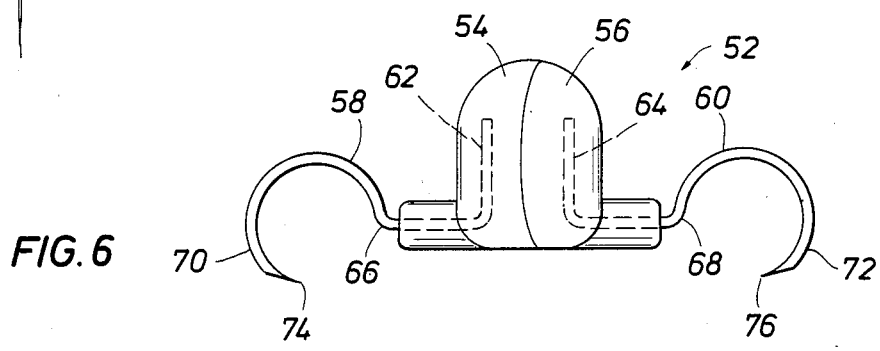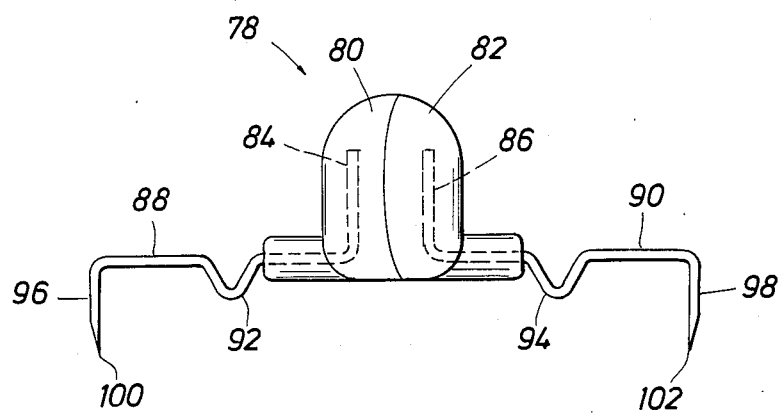

INTERLOCKING SURGICAL STAPLE ASSEMBLY

This is a continuation of application Ser. No. 465,246, filed Feb. 9, 1983, now abandoned.

RELATED INVENTION

This invention relates to the subject matter of application Ser. No. 411,470, filed by Applicant on Aug. 25, 1982, now U.S. Pat. No. 4,467,805 and entitled "Skin Closure Stapling Device for Surgical Procedures".

FIELD OF THE INVENTION

This invention relates generally to surgical procedures wherein incisions are closed by means of stapling following completion of the surgery. More specifically, the present invention concerns utilization of surgical staples having offset or curved skin penetrating elements which become hooked into the skin tissue to ensure that the skin at the incision is brought into non-overlapping, intimately engaging relation and to securely lock opposed strips of plastic locking material in interengaging relation with the skin tissue. The invention also concerns the provision of locking strip tissue surgical stapling apparatus which is affixed to the patient prior to incision, may be selectively opened to permit surgical incision, and may be closed in zipper-like fashion without suturing to quickly and efficiently close the incision.

BACKGROUND OF THE INVENTION

Following surgical procedures and for purposes of tissue repair, body openings formed by incision, tearing or cutting may be efficiently closed by securing the body tissue in intimate assembly. One method of skin closure is typically accomplished by suturing, where a curved needle with a thread-like suture attached through an eyelet thereof may be passed through the skin and may be secured by means of a surgical knot. Typically, a number of closely spaced sutures are required to accomplish efficient closure of a surgical incision.

Another method for accomplishing closure of a surgical incision or wound is to bring opposed skin portions into intimate assembly and then secure the same by means of surgical staples. Suitable stapling apparatus, typically referred to as a staple gun, is typically utilized to deform the staples in assembly with the skin tissue of the patient so that the staples function to maintain the opposed skin tissue in abutment to promote efficient healing.

One of the problems with application of staples to secure skin portions in assembly is the difficulty of maintaining opposed skin portions in abutting but non-overlapped relation. When the staples are deformed during installation, opposed skin tissues can easily become overlapped. The obvious result is improper healing and development of a surgical scar of undesirable configuration.

Through the use of sutures, the skin of the patient can be easily brought into proper abutting relation to ensure efficient healing. One of the problems with suturing, however, is that it is a time consuming procedure, thereby typically requiring the surgeon, the surgeon's staff and the and patient to spend more time under anesthesia in the operating theatre than is desired for efficient utilization of the operatory. It is desirable, therefore, to provide a means for accomplishing efficient and quick closure of the patient following completion of the surgical procedure to thereby minimize the time requirements for completion of the surgical procedure. It is also desirable to provide a system for accomplishing efficient closure of the patient and yet which also ensures that the skin of the patient is brought into intimate, non-overlapping, properly abutting relation through the use of stapling apparatus.

During a surgical procedure a surgical drape is employed to cover the surgical area and defines a slit or opening through which the surgery proceeds. The entire drape is typically provided with an adhesive backing and is applied to the surgical area prior to surgery. The main purpose of this to prevent infection. During surgery, blood can cause the edge of the drape to dissect from the incision site. Once this happens it is easy for infection to develop. This defeats the purpose of the drape for the drape is utilized to eliminate or minimize contamination of the incision that might cause infection. It is desirable therefore to provide means for positively securing a surgical drape to the body of the patient, thus exposing the site of the incision and preventing it from peeling off or otherwise becoming misaligned as the surgical procedure is being conducted.

SUMMARY OF THE INVENTION

It is a primary feature of the present invention to provide a novel apparatus for accomplishing quick and efficient closure of skin tissue by a surgical stapling procedure.

It is an even further feature of the present invention to provide a novel interlocking surgical staple assembly which is assembled to the skin and sub-skin tissues of the patient prior to incision and which positions the skin and sub-skin tissues in optimum position for efficient healing.

It is also a feature of this invention to provide a novel interlocking surgical staple assembly which may be quickly and efficiently reopened and reclosed as desired by the surgeon.

It is another feature of this invention to provide a novel interlocking surgical staple assembly employing surgical staples which are particularly designed to establish efficient skin support in the immediate vicinity of the incision to thereby effectively prevent any possibility of skin overlap as the staple assembly is manipulated to close the incision.

It is an even further feature of the present invention to provide a novel interlocking surgical staple assembly which incorporates surgical staples of particular design with a portion thereof functioning as a fulcrum or pivot about which the skin penetrating elements thereof rotate during staple gun bending, thereby causing the skin penetrating elements to move along an accurate path as they dip into the patient's tissue during stapling.

It is another feature of this invention to provide a novel interlocking staple assembly employing skin penetrating elements which establish hooked engagement with the skin and sub-skin tissue of the patient and therefore prevent inadvertent disengagement of the staple assembly when in the open condition thereof.

Among the several features of this invention is noted the provision of a novel method for assembly of a surgical drape to a surgery patient and which positively prevents the surgical drape from shifting relative to the incision as the surgical procedure is being conducted.

In accordance with the present invention, surgical staples are provided having an elongated staple bar capable of being bent intermediate the extremities thereof. The staples also incorporate a plurality of skin penetrating elements which extend transversely from the elongated staple bar and which are arranged in pairs at each extremity of the staple bar. The staple bar is capable of being bent between the centermost skin penetrating elements, causing the skin penetrating elements to be oriented in spaced, opposed relation when the staple is finished and properly installed to close the incision of the patient. The opposed pairs of skin penetrating elements maintain the skin and adjacent body tissue of the patient in intimate, non-overlapping relation to thus provide for efficient healing of the skin and body tissue and ensuring against development of an undesirably shaped scar at the incision.

For efficient closure of the surgical incision, the present invention incorporates a pair of elongated flexible locking strips, each of which incorporates elongated locking projections and grooves which interfit in interlocking relation so as to define a separatable closure. Each of the locking strips may be composed of a flexible plastic material such as polyethylene, for example. The locking strips may be brought into assembly or separated by manual application of force, if desired. Each of the elongated locking strips may have an opening tab attached thereto for the purpose of facilitating manual selective separation thereof for as much of the length of the locking strips as necessary to expose a desired length of the skin of the patient for the incision.

A plurality of half-staples are secured in spaced relation along each of the locking strips. The half-staples correspond when the locking strips are in assembly to define staple assemblies which are engaged into the skin and body tissues of the patient to establish structural interconnection with the skin and body tissues before the surgical incision is made. The flexible locking strips are unlocked and separated along a portion thereof to permit the incision to be made. Following the surgical procedure, the locking strips are brought into interlocking assembly to thereby force the skin and body tissues of the patient into intimate proper related assembly at the incision. The locking strips are pliable thus permitting bending to conform the staple assembly for an incision of any desired configuration.

Each of the half-staples defines a retainer portion which is embedded in or otherwise secured to respective ones of the locking strips. The half-staples also include an intermediate portion, part of which is intended to lie in generally parallel relation with the skin of the patient. The intermediate portion is intended to be bent by stapling apparatus as the staple assembly is applied to the patient. The intermediate portion of each half-staple will be formed to define an offset where the bending activity takes place during stapling operations. The terminal portion of each half-staple is defined by a skin penetrating element which is sharp pointed and capable of penetrating the skin of the patient and the body tissue immediately beneath the skin. The skin penetrating element extends transversely to the intermediate portion and is oppositely oriented as compared to the transverse locking projection. The skin penetrating element is so related to the intermediate portion that, during the bending activity of stapling, the sharp point thereof traverses a substantially arcuate path into the skin and sub-skin tissue at a location spaced from the incision and through the sub-skin tissue to a point in close proximity to the skin and the incnsion. Upon separation of the locking strips the individual half-staples will remain "hooked" into the tissue of the patient thereby preventing During application to the patient the staple may be employed to staple a disposable surgical drape to the skin of the patient, thereby maintaining the surgical drape in optimum position throughout the surgical procedure. Afterwards, the surgical drape may be readily torn away from the staples and disposed of without disturbing the staples.

Through utilization of the skin opening and closure apparatus of the present invention, surgical procedures are conducted as follows: An elongated staple assembly is provided having a pair of elongated locking strips which are maintained in interlocked assembly. Extending from the locking strips are half-staples as described above, arranged in spaced relation along the length of the assembled locking strips. Prior to making the incision in the skin of the patient, the interlocked staple assembly is positioned with the assembled locking strips located immediately over the site of the intended incision. The locking strips may also overlap the incision edges of a disposable surgical drape. A stapler tool is then utilized to deform the staples of the staple assembly and thus cause the skin penetrating elements thereof to penetrate the skin and traverse arcuate paths through the sub-skin tissue so that the points of the finished staples are located immediately below the skin and in juxtaposed relation with the incision. The staples thereby establish a stapled, retaining relationship of hooked character with the skin and the body tissues immediately below the skin. After the interlocked staple assembly has been attached to the patient at the site of the incision, the surgeon will accomplish separation of the interlocking strips to thereby expose the skin of the patient immediately below the interlocked strips. The locking strips may be separated initially at the intermediate portion thereof while the end portions remain in interlocked assembly. The incision may then be made and the surgical procedure conducted. After completion of the surgical procedure, closure of the skin of the patient is accomplished simply by moving the locking strips together and applying sufficient mechanical pressure to cause the grooves and ridges thereof to become mechanically interlocked. Because of the stapled relationship of the strips to the skin of the patient, this movement causes the skin to be brought into intimately assembled non-overlapping relation to permit healing. Leakage of body fluid is permitted at the incision to prevent the development of trapped fluid which might cause infection.

If desired, the interlocking staple assembly may be provided with a mechanical opening and closing device which accomplishes opening and closing of the device in zipper-like fashion. Following completion of the surgical procedure, the incision may, therefore, be closed in a few seconds time as compared with many minutes of time ordinarily required for suturing.

BRIEF DESCRIPTION OF THE DRAWINGS

So that the manner in which the above-recited features of the present invention, which will become apparent, are attained and can be understood in detail, more particular description of the invention, briefly summarized above, may be had by reference to the embodiments thereof which are illustrated in the appended drawings, which drawings form a part of this specification.

It is to be noted, however, that the appended drawings illustrate only typical embodiments of the invention and are therefore not to be considered limiting of its scope, for the invention may admit to other equally effective embodiments.

In the Drawings:

Figure 1:
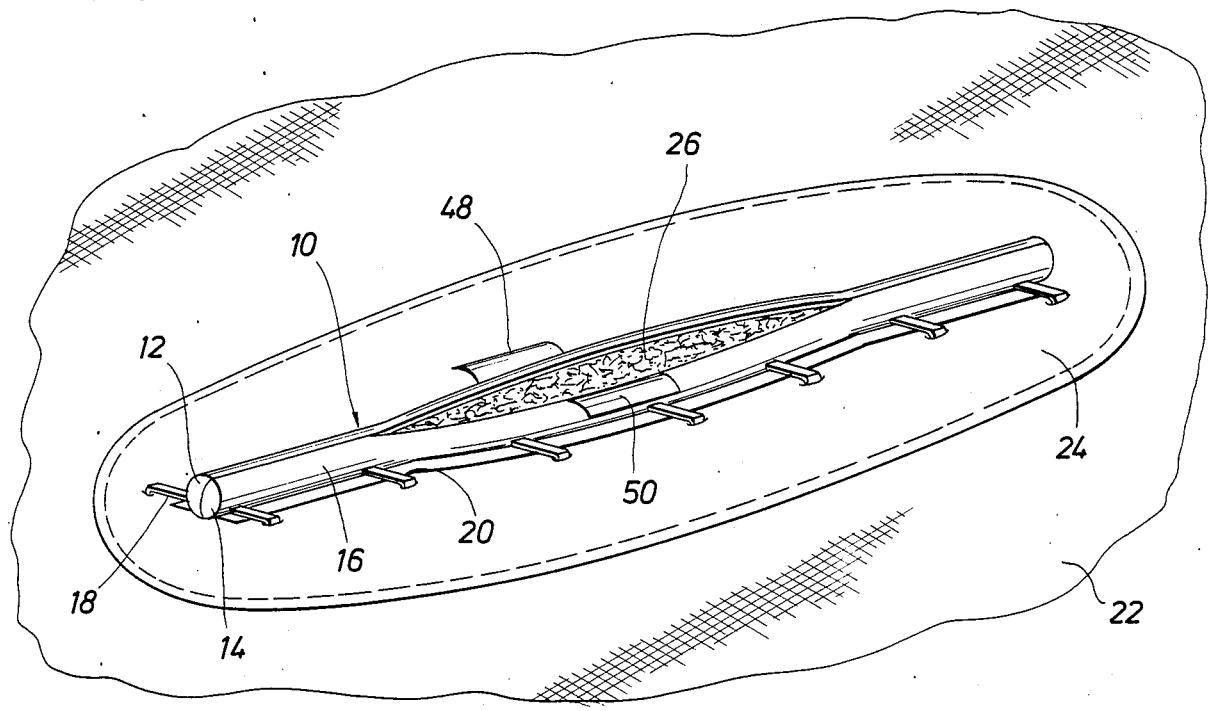

The present invention, both as to its organization and manner of operation, together with further objects and advantages thereof may best be understood by way of illustration and example of certain embodiments when taken in conjunction with the accompanying drawings in which:

FIG. 1 is a pictorial representation of an interlocking surgical staple assembly constructed in accordance with this invention and illustrating stapling of a surgical drape to the skin of a patient.

Figure 2:
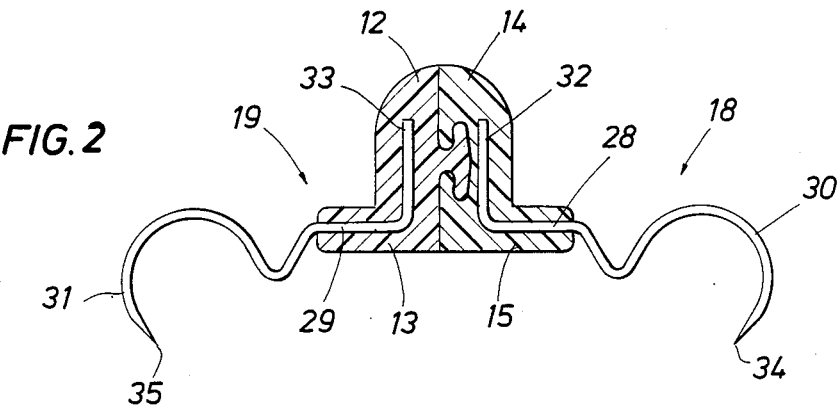

FIG. 2 is a cross-sectional view representating an interlocking and separatable surgical staple assembly constructed in accordance with the present invention.

Figure 3:
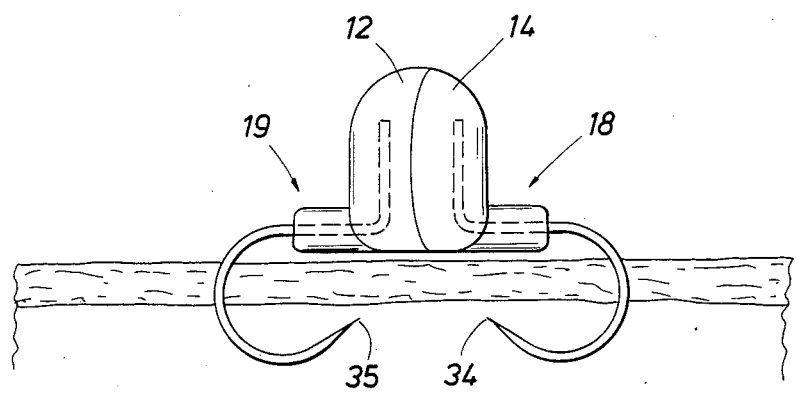

FIG. 3 is a cross-sectional view illustrating the staple assembly of FIG. 1 in its stapled form relative to the skin and sub-skin tissue of a patient and prior to the incision of a surgical procedure.

FIG. 4 is a cross-sectional view illustrating spearation of the locking strips of the staple assembly of FIG. 2 to permit the surgical incision.

FIG. 5 is a cross-sectional view illustrating relocking of the locking strips upon completion of the surgical procedure to close the incision.

FIG. 6 is a cross-sectional view illustrating an interlocking surgical staple assembly representing another embodiment of this invention.

FIG. 7 is a cross-sectional view illustrating an interlocking surgical staple assembly representing a further embodiment of this invention.

DETAILED DESCRIPTION OF PREFERRED EMBODIMENTS

Referring now to the drawings and first to FIG. 1, a staple assembly is illustrated generally at 10 which comprises a pair of elongated locking strips 12 and 14 which are placed in interlocking assembly to form a locking strip 16. Each of the locking strips 12 and 14 are composed of flexible plastic material such as polyethylene, silicone or any other suitable material having the capability of being sterilized for use for surgical procedures. The locking strips are pliable, allowing them to be bent or formed according to the configuration of the incision to be made. This pliability also permits opening of the locking strips at the central portion thereof as will be more clearly evident below. Locking strips 12 and 14 incorporate interengaging ridges and grooves of any suitable design which permit the locking strips to be retained in interlocked assembly and also permit the locking strips to be separated for conduct of a surgical procedure and then brought back to interlocking relation following the surgical procedure. The staple assembly further incorporates a plurality of half-staples such as shown at 18 and 20 which are of generally identical construction and which are secured to respective ones of the locking strips 12 and 14. As shown, a plurality of spaced half-staples 18 and 19 is secured to the locking strip 12 while a plurality of spaced half-staples 20 is secured to the locking strip 14.

In many cases, surgical drapes tend to peel off during surgical procedures, causing contamination that may results in the development of infection. To solve this problem, surgical drapes have been developed having adhesive material on the backing which secures the drape in place. The adhesive material is intended to adhere to the skin of the patient to prevent slipping or peeling of the surgical drape. It has been found, however, that body fluids and blood of the patient and medicaments utilized during surgical procedures tend to dissect the adhesive material, thereby allowing the surgical drape to slip and may cause infection. In order to overcome the tendency of a surgical drape to peel off, disposable surgical drapes are provided as shown in FIG. 1 at 22 which have a frangible portion 24 through which the surgical procedure is conducted. The interlocking staple assembly 10 is positioned so that the staple elements 18 and 20 penetrate the frangible portion 24 of the drape. A stapling machine, typically referred to as a staple gun, is then utilized to attach the staples through the frangible portion of the surgical drape and then through the skin and sub-skin tissue of the patient. The surgical drape is therefore affixed to the skin of the patient by the stapling operation. After the surgical procedure has been completed, the frangible portion of the surgical drape will simply be torn away from the staples, leaving the interlocking staple assembly in secured relation with the skin and sub-skin tissue of the patient.

As shown in FIGS. 2 through 5, each of the half-staples incorporates a central portion 28 and 29 having a transversely projecting skin penetrating element such as shown at 30 and 31 for the purpose of penetrating the skin and the body tissue of the patient immediately beneath the skin. The half-staples 18 are positioned in substantially evenly spaced relation along the length of the locking strips 12 and 14. The locking strips and thus the locking strip assembly 16 may be of any suitable length appropriate the accomplish the desired surgical procedure. If desired, the locking strip assembly may be provided in a suitable length for accomplishment of most surgical procedures, and may then be cut to the desired length in the operatory for the particular surgical procedure involved. If desired, the locking strip assembly may be added to the original strip assembly to extend the incision.

Each of the half-staples is also provided with a transversely oriented locking projection such as shown at 32 and 33 in broken line in FIGS. 3–5. The locking projections are retained within the material of the locking strips, thus securing the staple halves in opposed, spaced relation. Locking strip flanges 13 and 15 provide additional structural support for the half-staples and prevent the development of staple bar marks in the seat tissue that is developed during the healing process.

The intermediate portions 28 and 29 of the staple halves 18 and 19 are intended to be deformed by bending during stapling operations. The staple gun will bend the intermediate portions of each half-staple thereby causing the skin penetrating elements 30 and 31 thereof to traverse the skin and sub-skin tissues of the patient. After being deformed during stapling each of the half-staples 18 and 19 will be essentially in the form shown in FIG. 3.

Since the locking strips 12 and 14 are intended for separation at least along a major portion of the length thereof to permit access to the skin tissue of the patient for surgery, it is necessary that each of the half-staples be capable of efficient retention to the skin and sub-skin tissues of the patient after separation of the locking strips has occurred. For this reason, it is desired that each of the half-staples be capable of establishing a "hooked" retaining relation with the skin and sub-skin tissues of the patient. This hooked relationship prevents inadvertent disassembly of the half-staples from the tissues of the patient while the surgical procedure is being conducted and thereby also ensures that the locking strips may be relocked to accomplish closing of the incision after the surgical procedure has been completed.

As illustrated in FIG. 1, prior to making the incision for a surgical procedure, a stapling mechanism or stapling gun is employed to deform the staples in the manner shown in FIGS. 3-5 to thus accomplish installation of the staple assembly 10 in assembly with the skin and sub-skin tissue of the patient. When assembled to the skin of the patient, as shown in FIG. 3, each of the half-staples is deformed and embedded in retaining relationship with the skin. During deformation of the half staples by the stapling gun, the half-staples are bent in such manner that the sharp points 34 and 35 thereof move in arcuate manner through the skin and sub-skin tissue of the patient. The sharp points penetrate the skin tissue and move downwardly and inwardly toward the incision in arcuate manner. Before reaching the line of the intended incision the points 34 are moved upwardly until they reach a slightly spaced position immediately beneath the skin. The final positions of the points 34 and 35 after bending of the staple halves by the staple gun are shown in FIG. 3.

As illustrated in FIG. 4, the locking strips 12 and 14 are separated along the length thereof by withdrawing a locking ridge portion 36 of locking strip 12 from an undercut locking groove 38 formed in locking strip 14. The locking ridge 36 incorporates opposed locking flanges 40 and 42 which are capable of yielding as the locking ridge is forced into the locking groove 38. Likewise, locking strip 14 defines flexible portions 44 and 46 which define a restricted opening for the undercut locking groove 38. These flexible portions will also yield to some extent as the locking ridge 36 is forced into the locking groove. The flanges 40 and 42 and the flexible portions 44 and 46 would also yield to some extent as the locking ridge is withdrawn from the locking groove during separation of the locking strips. The assembled relationship of the locking ridge and locking groove is illustrated in FIG. 2.

Ordinarily, to conduct a surgical procedure, the interlocking surgical staple assembly will be first attached to the skin and sub-skin tissue of the patient with the central portion of the locking strip located immediately over the line of the intended incision. Thereafter, the locking strip will be at least partially separated thereby allowing the surgeon to gain access to the skin tissue for incision with a scalpel. Ordinarily, the locking strips will be separated only at the intermediate portions thereof thereby allowing the end portions to remain in locking assembly. After termination of the surgical procedure, this partially assembled relationship of the locking strips will enable them to be simply and efficiently locked along the entire length thereof simply through application of manual pressure to opposed sides of the locking strips. To accomplish separation of the intermediate portion of the locking strips, each of the strips is provided with pull tabs such as shown at 48 and 50 in FIG. 1. The surgeon or surgeon's assistant will grasp the pull tabs 48 and 50 either manually or with aid of forceps or other suitable instruments and will apply opposed force to the pull tabs. This opposed force will cause separation of the intermediate portion of the locking strips. Force will be applied sufficiently to separate the locking strips along a desired length thereof, leaving the end portions of the locking strips in intimate locked assembly. If the opening defined by the separated locking strips is of insufficient length, the surgeon may simply apply manual force to the pull tabs 48 and 50 and smply pull them further apart to gain additional length of opening for the incision. Forceps may be applied to opposed portions of the strips themselves to separate them as necessary to gain sufficient length for the incision. By ensuring that the end portions of the locking strips remain in interlocked assembly, ease of closing is facilitated to thus accomplish closing of the incision. The surgeon will simply apply manual pressure along the length of the locking strips in zipper-like fashion to cause the locking ridges 36 to fully engage the locking grooves along the full length thereof. In the event additional length of incision is desired after an initial incision has been made, another interlocked staple strip may be positioned at the end of the installed staple strip and stapled in place. After this has been done, the bead and groove of the additional strip is opened, permitting the surgeon to extend the incision and proceed with the surgery.

As shown in FIG. 4, the locking strips 12 and 14 are separated and the surgical incision has been made. As shown in FIG. 5, the locking strips 12 and 14 have been brought into intimate interlocked assembly thus closing the incision. During the surgical procedure, the individual locking strips remain in positively hooked assembly with the skin and sub-skin body tissues of the patient as illustrated in FIG. 4. There is no tendency of the locking strips to rotate and thus cause the skin penetrating elements thereof to become disengaged from their hooked relationship with the skin and sub-skin body tissues of the patient.

The present invention may take other suitable forms without departing from the spirit and scope of the present invention. Two embodiments of the invention are represented by the cross-sectional views of FIGS. 6 and 7. As shown in FIG. 6, an interlocking surgical staple assembly is illustrated generally at 52 which incorporates locking strips 54 and 56 which may be of substantially identical configuration as compared to the locking strips 12 and 14 of FIG. 2. It should be borne in mind that the locking strips may also take many other suitable forms without departing from the spirit and scope of the present invention. Half staple elements 58 and 60 are provided which incorporate transversely oriented locking projections 62 and 64 which are embedded within the material defining the locking strips 54 and 56 respectively. The half-staples 58 and 60 incorporate intermediate portions which are offset at 66 and 68 so as to define bend portions capable of being bent by a staple gun. The half-staples also define arcuate skin penetrating elements 70 and 72 having sharp points 74 and 76 for penetrating the skin and sub-skin tissue of the patient. As bending takes place at points 66 and 68 along the length of the half-staples the arcuate skin penetrating portions 70 and 72 move in arcuate manner through the skin and sub-skin tissue. After bending is complete by the staple gun, the sharp points 74 and 76 will be positioned in closely spaced relation immediately beneath the skin tissue of the patient essentially as shown in FIG. 4.

As shown in FIG. 7, the interlocking staple assembly may take another form as shown generally at 78 incorporating elongated locking strips 80 and 82 of substantially the same form and function as shown at 12 and 14 in FIG. 2. Transverse locking projections 84 and 86 are embedded within respective locking strips 80 and 82 thereby supporting half-staples 88 and 90 in assembly with the locking strips. The half-staples 88 and 90 define offset portions 92 and 94 where bending activity takes places as the staple halves are bent during assembly to the body tissue of the patient. The half-staples also define skin penetrating elements 96 and 98 which are sharply bent and oriented at approximately 90° in relation to the intermediate portion thereof. The terminal portions of the skin penetrating elements define sharp points 100 and 102. Upon bending of the half-staples at the offset areas 92 and 94 the sharp points 100 and 102 of the skin penetrating elements will move in arcuate manner downwardly through the skin and sub-skin tissue of the patient. Continued bending at the offset portions 92 and 94 of the half-staples will move the skin penetrating elements arcuately to a spaced location immediately beneath the skin tissue of the patient in the manner shown in FIG. 3. This arcuate movement of the skin penetrating points will result in the development of a hooked relationship of the half-staples in the skin and sub-skin tissue of the patient. Upon separation of the locking strips therefore there will be no tendency for the staple halves to become inadvertently disassembled from the tissue of the patient.

One of the more important aspects of accomplishing a staple-closed incision of skin tissues following surgery is that the skin tissue often becomes overlapped to some extent. This overlapping skin tissue permits bacterial collection in the area of skin overlapping, thus increasing the possibility of infection at the site of the incision. Further, healing of overlapped skin tissues often develops scar tissue that is unsightly and thus objectionable to the patient. By ensuring that each of the half-staples establishes a hooked relationship with the skin and sub-skin tissue of the patient and by causing positioning of the skin penetrating points of the half-staples in closely spaced relation with the incision and immediately beneath the skin tissue of the patient there will be no tendency for skin overlapping to take place as the incision is closed. Upon bringing the locking strips into interlocked assembly as shown in FIG. 5 the closely spaced skin penetrating points will cause the opposed skin tissue to be forced into abutting, nonoverlapping relation. The surgical incision is therefore capable of draining efficiently thus preventing development of infection. The nonoverlapping, abutting relationship of the skin tissue causes the development of minimal scar tissue. By providing the half staples with offset portions the stapling activity causes the offset portions to establish a pivot or fulcrum about which the skin penetrating portions of the half-staples are rotated. The skin penetrating elements therefore move in arcuate manner through the skin and sub-skin tissue of the patient and do not tend to force the skin tissue such that an overlapping relation would otherwise be establbished upon closure of the incision by means of the locking strips. Although the figures of the present invention illustrate a configuration of the locking strips and various configurations of the half-staples, these figures are by no means restrictive of the possible configurations thereof. The locking strips and the half staples may take any one of a number of suitable forms within the spirit and scope of the present invention.

In view of the foregoing it is therefore seen that my invention is one well adapted to attain all of objects and advantages hereinabove set forth together with other advantages which will become obvious and inherent from a description of the apparatus itself. It will be understood that certain combinations and subcombinations are of utility and may be employed without reference to other features and subcombinations. This is contemplated by and is within the scope of the present invention.

What is claimed is:

1. A skin opening and closure device for surgical procedures, comprising:
    (a) first and second elongated locking strips having mating strip locking means formed along the length thereof, said locking strips being capable of interlocking assembly and capable of being separated and reassembled;
    (b) a plurality of spaced half-staple means being secured to each of said locking strips and being in closely spaced relation along the length thereof, said half-staple means each defining arcuately curved skin penetrating portions having point means inclined angularly toward one another and adapted to be embedded into the skin of a patient in preparation for surgery, said skin penetration portions being preformed with bending sections such that deformation of said half-staple means by staple installation apparatus at said bending sections causes said arcuately curved skin penetrating portions and said point means to penetrate the skin, traverse an arcuate path deeply into the skin tissue such that said point means are positioned immediately beneath the surface of the skin and adjacent the incision line; and
    (c) with said half-staple means embedded in the skin of the patient, said locking strips being separatable to expose the skin of the patient to permit incision and capable of being forced into interlocking assembly to close the incision and bring the skin tissue at the incision into tightly abutting relation.

2. A skin opening and closure device as recited in claim 1, wherein:
    each of said half-staple means is formed to define an offset between said locking strips and said skin penetrating elements, bending said half-staple means at said offset causing said skin penetrating portions to traverse an arcuate path through the skin and sub-skin tissue of the patient.

3. A skin opening and closure device as recited in claim 1, wherein:
    said locking strips are each formed of yieldable plastic material and, when in interlocked relation, are capable of being selectively separated to expose as much skin as is desirable for accomplishing the surgical procedure, said skin penetrating portions of said half-staple means functioning in hook-like manner to prevent staple separation from the skin tissue when said locking strips are separated.

4. A skin opening and closure device as recited in claim 1, including:
    opening tab means being secured to each of said first and second elongated locking strips and being manually manipulated to accomplish forcible separation of said elongated locking strips from the interlocked relation thereof.

5. A skin opening and closure device as recited in claim 1, wherein:
    said half-staple means define straight intermediate portions with locking portions extending transversely therefrom and being embedded in said elongated locking strips, said half-staple means further defining arcuate skin penetrating elements projecting transversely from said straight intermediate portions.

6. A skin opening and closure device as recited in claim 1, wherein:
said first and second elongated locking strips are capable of being forced into interlocking assembly and separated by application of manual force thereto.

7. A skin opening and closure device as recited in claim 1, wherein:
each of said half-staple means defines a bending point about which said skin penetrating element rotates, causing said skin penetrating element to traverse a generally arcuate path through the skin and sub-skin tissue of the patient.

8. A skin opening and closure device for surgical procedures, comprising:
(a) first and second elongated locking strips capable of being placed in interlocking assembly and capable of being separated and relocked;
(b) a plurality of half-staple means being secured to each of said locking strips and being closely spaced along the length thereof, said half-staple means each defining elongated staple bar means positioned in generally coextensive relation, said staple bar means each defining bending points positioned in spaced relation with one another and positioned immediately adjacent the respective elongated locking strip; and
(c) arcuately curved skin penetrating elements extending from each of said staple bar means and defining sharp skin penetrating points integral therewith and at the free extremities thereof, said skin penetrating elements being of hook-like configuration with said free extremities thereof being positioned in arcuate angular relation with said staple bar means and positioned in converging relation with one another, upon deformation of said half-staple means at said bending points, said skin penetrating points penetrating the skin of the patient and traversing an arcuate path through the skin and sub-skin tissue of the patient, bringing the opposed skin penetrating points close together immediately beneath the surface of the skin and adjacent to an intended incision line.

* * * * *